United States Patent
Drysdale et al.

(10) Patent No.: US 8,513,454 B2
(45) Date of Patent: Aug. 20, 2013

(54) PREPARATION OF (PHOSPHONYL) AROMATIC DIESTERS AND ACIDS

(75) Inventors: Neville Everton Drysdale, Newark, DE (US); Fredrik Nederberg, Greenville, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 131 days.

(21) Appl. No.: 13/314,664

(22) Filed: Dec. 8, 2011

(65) Prior Publication Data

US 2013/0150612 A1    Jun. 13, 2013

(51) Int. Cl.
*C07C 67/08* (2006.01)
*C07C 69/75* (2006.01)

(52) U.S. Cl.
USPC ............ 560/64; 560/1; 560/3; 560/8; 560/18

(58) Field of Classification Search
USPC ......................................... 560/1, 3, 8, 18, 64
See application file for complete search history.

(56) References Cited

U.S. PATENT DOCUMENTS

| | | | |
|---|---|---|---|
| 3,962,232 | A | 6/1976 | Koppel |
| 4,131,594 | A | 12/1978 | Nakamura et al. |
| 5,616,659 | A | 4/1997 | Deviney et al. |
| 2004/0024255 | A1 | 2/2004 | Wang et al. |
| 2011/0060116 | A1 | 3/2011 | Drysdale et al. |
| 2011/0218353 | A1 | 9/2011 | Drysdale et al. |

FOREIGN PATENT DOCUMENTS

| | | |
|---|---|---|
| EP | 1153953 A1 | 11/2001 |
| WO | 2010132332 A1 | 11/2010 |

OTHER PUBLICATIONS

Related Application, US Application Serial Number Not Yet Assigned, (Neville Everton Drysdale et al., Filed December 7, 2011).
Van Krevelen, Some Basic Aspects of Flame Resistance of Polymeric Materials, Polymer, vol. 16 (1975), pp. 615-620.
Qreshi et al., Synthesis and Characterization of Novel 6-Substituted 4-Phenyl-6H-Dibenz[C,E][1,2]Oxaphosphorins, J. Chem Research, vol. S (1998), p. 355.
Chen et al., Aryl Polyphosphonates: Useful Halogen-Free Flame Retardants for Polymers, Materials, vol. 3, (2010), pp. 4746-4760.
Li et al., Synthesis, Characterization, and Polymerization of Brominated Benzoxazine Monomers and Thermal Stability/Flame Retardance of the Polymers Generated, Polym. Adv. Technol., vol. 21 (2010), pp. 229-234.

*Primary Examiner* — Johann R Richter
*Assistant Examiner* — Blaine G Doletski

(57) ABSTRACT

The composition of a (phosphonyl) aromatic compound represented by

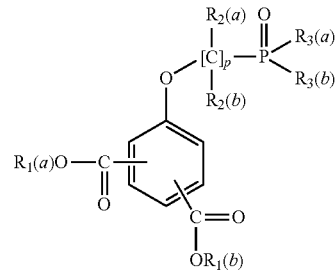

is provided. In this composition, $R_1(a)$ and $R_1(b)$ are each independently H, $C_nH_{2n+1}$, phenyl or benzyl; $R_2(a)$ and $R_2(b)$ are each independently H, $C_nH_{2n+1}$, phenyl or benzyl with the proviso that no more than one $R_{2(a)}$ and no more than one $R_{2(b)}$ can be phenyl or benzyl; $R_3(a)$ and $R_3(b)$ are each independently $C_nH_{2n+1}$, phenyl or benzyl; and, n is an integer of 1-10; and p is an integer of 1-10. The disclosed composition can find utility in improving flame retardancy of polyesters, aramids and nylons.

4 Claims, No Drawings

PREPARATION OF (PHOSPHONYL) AROMATIC DIESTERS AND ACIDS

FIELD OF INVENTION

The present invention is directed to (phosphonyl)aromatic diester and acid compounds and derivatives thereof. The compounds disclosed can have utility as flame retardants in various types of polymers.

BACKGROUND

Natural and synthetic polymers are being increasingly used under ever more demanding environmental conditions. Flame retardants are commonly used to reduce combustibility of polymeric materials, such as polycarbonates, polyesters and polyamides, has therefore become a pivotal part of the development and application of new materials. (Chen, L., and Wang, Y., Materials, 3: 4746-4760, 2010 and WO2010/132332A1).

Increasing flame retardancy of polymers has been addressed through addition of various flame retardants. For example organophosphorus compounds have been used as flame retardants for polyesters, polyamides and polycarbonates (WO2010/132332A1). Aryl polyphosphonates have been used as flame retardants for polycarbonates and polyamides (Chen, L., supra).

Polyesters such as polytrimethylene terephthalate (PTT), polyethylene terephthalate (PET) and polybutylthylene terephthalate (PBT), find use in many application areas (such as carpets, home furnishings, automotive parts and electronic parts) which require a certain level of flame retardancy. PTT provides desirable attributes such as stretch and recovery, resiliency and stain resistance desirable in face fibers of carpets and is preferred to PET and PBT in such applications. In some carpet construction of PTT fibers do not pass certain standard flammability tests without the use of flame retardant additives.

A number of flame retardants available to date contain various types of halogens (U.S. Pat. No. 4,131,594) which are not environmentally acceptable. A need remains for new flame retardants, particularly non-halogenated flame retardants, for use in polymers.

SUMMARY OF THE INVENTION

The current invention provides a composition and a process for preparing of novel (phosphonyl)aromatic compounds that can improve the flame retardancy of polymers.

In one aspect, the present invention provides a composition comprising a (phosphonyl) aromatic compound represented by the structure (I)

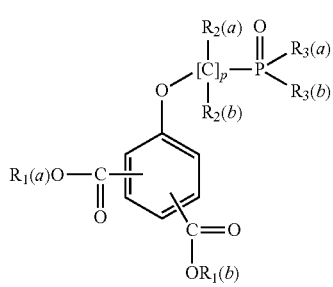

structure (I)

wherein,
$R_1(a)$ and $R_1(b)$ are independently H, $C_nH_{2n+1}$, phenyl or benzyl;
$R_2(a)$ and $R_2(b)$ are each independently H, $C_nH_{2n+1}$, phenyl or benzyl with the proviso that no more than one $R_{2(a)}$ and no more than one $R_{2(b)}$ can be phenyl or benzyl;
$R_3(a)$ and $R_3(b)$ are each independently $C_nH_{2n+1}$, phenyl or benzyl;
n is an integer of 1-10;
and,
p is an integer of 1-10.

In another aspect, the present invention provides a process for preparing a (phosphonyl)aromatic compound combining a halogenated(phosphonyl) compound represented by the structure (II)

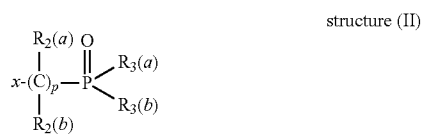

structure (II)

wherein,
$R_2(a)$ and $R_2(b)$ are each independently H, $C_nH_{2n+1}$, phenyl or benzyl with the proviso that no more than one $R_{2(a)}$ and no more than one $R_{2(b)}$ can be phenyl or benzyl;
$R_3(a)$ and $R_3(b)$ are each independently $C_nH_{2n+1}$, phenyl or benzyl;
x is Cl or Br;
x is O;
n is an integer of 1-10;
and,
p is an integer of 1-10;
and a phenolic diester compound represented by the structure (III)

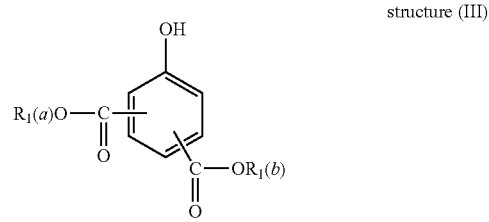

structure (III)

wherein,
$R_1(a)$ and $R_1(b)$ are each independently H, $C_nH_{2n+1}$, phenyl or benzyl;
in the presence of one or more bases catalysts with a pH range of 9-14 and one or more solvents while stirring under reflux in a nitrogen atmosphere.

In one aspect contacting the phenolic diester and the halogenated (phosphonyl) compound provides a (phosphonyl) aromatic diester.

In another aspect contacting the (phosphonyl)aromatic diester and an additional base in aqueous solution followed by heating overnight and precipitation by concentrated hydrochloric acid provides a (phosphonyl)aromatic diacid.

DETAILED DESCRIPTION

When a range of numerical values is provided herein, it is intended to encompass the end-points of the range unless specifically stated otherwise. Numerical values used herein have the precision of the number of significant figures provided, following the standard protocol in chemistry for significant figures as outlined in ASTM E29-08 Section 6. For example, the number 40 encompasses a range from 35.0 to 44.9, whereas the number 40.0 encompasses a range from 39.50 to 40.49.

As used herein, the term "(phenoxy)aromatic compound" refers to the compound of structure (I). The term "halogenated (phosphonyl) compound" refers to the compound of structure (II). The term "phenolic diester compound" refers to compound of structure (III).

In one aspect, the present invention provides a composition comprising a (phenoxy)aromatic compound represented by the structure (I)

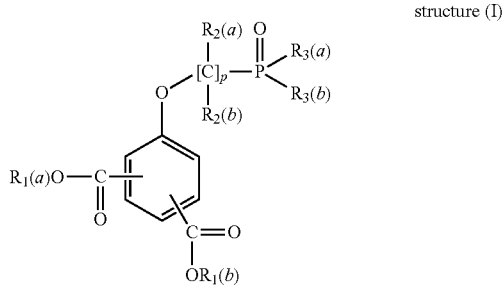

structure (I)

wherein, $R_1(a)$ and $R_1(b)$ are each independently H, $C_nH_{2n+1}$, phenyl or benzyl;

$R_2(a)$ and $R_2(b)$ are each independently H, $C_nH_{2n+1}$, phenyl or benzyl with the proviso that no more than one $R_2(a)$ and no more than one $R_2(b)$ can be phenyl or benzyl;

$R_3(a)$ and $R_3(b)$ are each independently $C_nH_{2n+1}$, phenyl or benzyl;

n is an integer of 1-10;

and, p is an integer of 1-10.

In an embodiment, $R_1(a)$ and $R_1(b)$ are the same.

In another embodiment, $R_2(a)$ and $R_2(b)$ are the same.

In yet another embodiment, $R_3(a)$ and $R_3(b)$ are the same.

In yet another embodiment, $R_1(a)$ and $R_1(b)$ are the same.

In yet another embodiment, $R_2(a)$ and $R_2(b)$ are the same.

In yet another embodiment, $R_3(a)$ and $R_3(b)$ are the same.

In yet another embodiment $R_1(a)$ and $R_1(b)$ are H or $C_nH_{2n+1}$ or methyl.

In yet another embodiment $R_1(a)$ and $R_1(b)$ are H and $R_3(a)$ and $R_3(b)$ are methyl.

In yet another embodiment $R_3(a)$ and $R_3(b)$ are methyl.

In yet another embodiment $R_1(a)$, $R_1(b)$, $R_3(a)$ and $R_3(b)$ are methyl.

In yet another embodiment $R_2(a)$ and $R_2(b)$ are $C_nH_{2n+1}$ or H.

As can be noted in the structures above, the substituents can be attached to the aromatic ring at any point, thus making it possible to have ortho-, meta- and para-substituents as defined above.

In an aspect, the present invention provides a process for preparing the (phenoxy)aromatic compounds.

In one embodiment, the (phenoxy)aromatic compound is prepared by contacting a halogenated (phosphonyl) compound of structure (II) wherein p, $R_2(a)$, $R_2(b)$, $R_3(a)$ and $R_3(b)$ are as defined above and x is O,

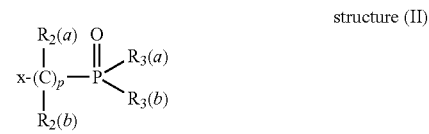

structure (II)

with a phenolic diester compound of structure (III) wherein $R_1(a)$ and $R_1(b)$ are as defined above,

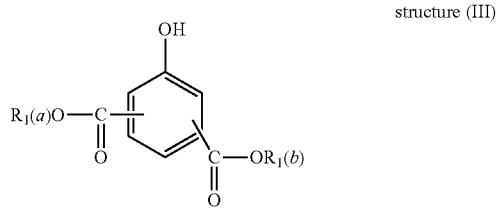

structure (III)

one or more solvents and a base under reflux while stirring after which the reaction mixture is maintained under reflux for 48 hours until the desired yield of reaction is achieved.

In one embodiment, the reaction is performed at a temperature in the range of 25-250° C. In a further embodiment the reaction is performed at a temperature in the range of 25-100° C. The reaction mixture is held at the reaction temperature until the desired yield of reaction is achieved, and the reaction mixture is subsequently cooled.

The reaction of forming the (phenoxy)aromatic is catalyzed by one or more base catalysts. Any catalyst that is capable of deprotonating phenol can be used. That is, a suitable catalyst is any catalyst having a pKa greater than that of phenol (9.95, using water at 25° C. as reference). Suitable catalysts include, but are not limited to, sodium methoxide, calcium hydride, sodium metal, potassium methoxide, potassium t-butoxide, potassium carbonate, benzyltrimethyl-ammonium hydroxide, and sodium carbonate. Preferred are potassium t-butoxide, potassium carbonate, sodium carbonate and benzyltrimethylammonium hydroxide.

The reaction for forming the (phenoxy)aromatic compound can be terminated at any desirable point by filtration to remove the catalyst.

Suitable solvents useful for the current process include, but are not limited to: aprotic solvents such as ethylacetate, toluene, xylenes, tetrahydrofuran and 1,4-dioxane.

In the practice of the process for preparing the (phenoxy) aromatic compound, a suitable halogenated phosphonyl compound and a suitable phenolic diester compound are contacted in the presence of one or more suitable solvents and one or more suitable bases until the reaction has achieved the desired degree of conversion. In one embodiment, the reaction is continued until no further product is produced over some pre-selected time scale. The required reaction time to achieve the desired degree of conversion depends upon the reaction temperature, the chemical reactivity of the specific reaction mixture components, and the degree of mixing applied to the reaction mixture, and can be readily determined by one skilled in the art. Progress of the reaction can be monitored using any one of a variety of established analytical methods, including, but not limited to, nuclear magnetic resonance spectroscopy, thin layer chromatography, and gas chromatography. When the desired level of conversion has been achieved, the reaction mixture is stopped, as described supra.

In one embodiment, the stopped reaction mixture is concentrated under vacuum, and rinsed with a solvent. Separation of the product thus produced can be effected by any method known to the skilled artisan such as, for example, distillation or column chromatography.

In one embodiment, the (phenoxy)aromatic diester compound formed can be converted into a (phenoxy)aromatic diacid by contacting the (phenoxy)-aromatic diester compound with one or more base catalysts and an aqueous solution to provide a reaction mixture. The reaction mixture is then stirred under reflux overnight. Following these steps, the reaction mixture is then cooled with concentrated hydrochloric acid and the precipitate can be filtered off and dried under vacuum.

The (phosphonyl) aromatic diesters compounds disclosed herein can be used as additives in polymeric systems, such as polyesters, aramids, and nylons, to improve the flame retardancy of these polymers.

A homopolymer of the (phosphonyl) aromatic diesters compounds comprise repeat units represented by structure IV

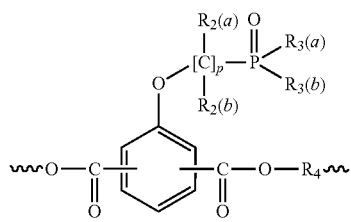

wherein $R_2(a)$ and $R_2(b)$ are each independently H, $C_nH_{2n+1}$, phenyl or benzyl with the proviso that no more than one $R_{2(a)}$ and no more than one $R_{2(b)}$ can be phenyl or benzyl;

$R_3(a)$ and $R_3(b)$ are each independently $C_nH_{2n+1}$, phenyl or benzyl;

$R_4$ is a $C_1$-$C_6$ alkylene radical;

n is an integer of 1-10;

and, p is an integer of 1-10.

In an embodiment, $R_1(a)$ and $R_1(b)$ are the same.

In another embodiment, $R_2(a)$ and $R_2(b)$ are the same.

In yet another embodiment, $R_3(a)$ and $R_3(b)$ are the same.

In yet another embodiment $R_1(a)$ and $R_1(b)$ are H or $C_nH_{2n+1}$ or methyl.

In yet another embodiment $R_1(a)$ and $R_1(b)$ are H and $R_3(a)$ and $R_3(b)$ are methyl.

In yet another embodiment $R_3(a)$ and $R_3(b)$ are methyl.

In yet another embodiment $R_1(a)$, $R_1(b)$, $R_3(a)$ and $R_3(b)$ are methyl.

In yet another embodiment $R_2(a)$ and $R_2(b)$ are $C_nH_{2n+1}$ or H.

In yet another embodiment R4 is propylene.

In one embodiment a homopolymer (structure V) of the (phosphonyl) aromatic diesters can be formed by reacting the diester compound with glycol in the presence of a catalyst.

The suitable catalyst for this reaction can be titanium (IV) butoxide, titanium (IV) isopropoxide, antimony trioxide, antimony triglycolate, sodium acetate, manganese acetate, and dibutyl tin oxide. The suitable glycol for this reaction can be ethylene glycol, 1,3-propanediol, 1,4-butanediol, longer aliphatic diols, branched polyols, or branched diols.

structure V

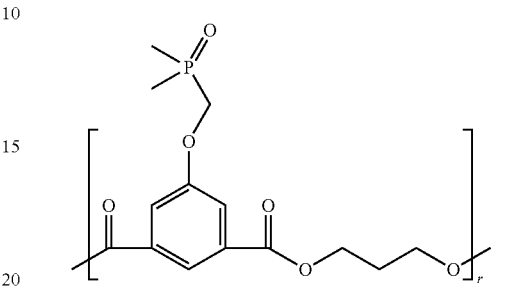

In another embodiment, the catalyst is Titanium(IV)isopropoxide. In yet another embodiment the glycol is 1,3-propanediol. The mixture of the (phosphonyl) aromatic diester, the catalyst and the glycol is stirred under nitrogen in the melt (solvent free) at a temperature within the range of from room temperature (20-25° C.) to the reflux temperature of the reaction mixture, preferably up to 180 to 240° C. for 1-2 hours, to condense methanol. Thereafter the mixture is further heated, preferably to a temperature within the range of 200 to 300° C., and evacuated and stirred during 2-4 hours, to remove the excess glycol and thereby form a polymer.

In another embodiment a copolymer (structure VII) comprising the repeat units represented by the structure IV can be formed by reacting the compound of structure IV with a glycol and a second diester/diacid compound represented by the structure VI.

wherein

Q is a benzene radical or an ethylene radical or a tetramethylene radical or a naphthalene radical or an octylene radical.

in the presence of a catalyst.

Suitable diesters or diacids include but not limited to dimethyl terephthalate, terepthalic acid, 2,6-napthalene dicarboxylic acid, dimethyl 2,6-napthalenedicarboxylate, succinic acid, adipic acid, and sebacid acid. The suitable catalyst for this reaction can be titanium (IV) butoxide, titanium (IV) isopropoxide, antimony trioxide, antimony triglycolate, sodium acetate, manganese acetate, and dibutyl tin oxide. The suitable glycol for this reaction can be ethylene glycol, 1,3-propanediol, 1,4-butanediol, longer aliphatic diols, branched polyols, or branched diols. In another embodiment, the catalyst can be Titanium(IV)isopropoxide. Structure VII is shown below.

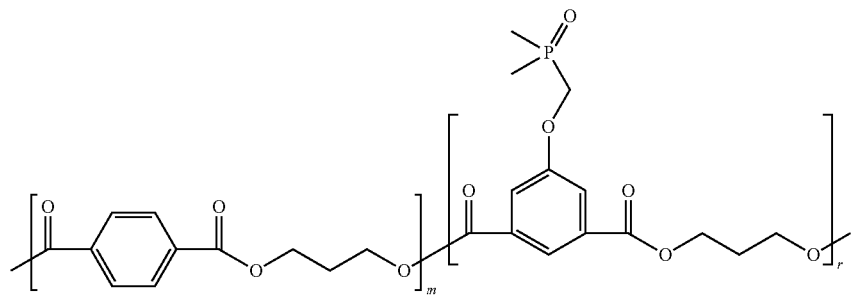

In one embodiment for preparing the copolymer dimethyl 5-((dimethylphosphoryl)methoxy)-isophthalate can be reacted with 1,3-propanediol, and dimethylterepthalate in the presence of Tyzor as the catalyst.

EXAMPLES

The invention is further described but not limited by the following specific embodiments thereof.

Materials

The chemicals and reagents were used as received in the Examples as follows:

Dimethyl-5-hydroxy isophthalate was obtained from Aldrich.

(Chloromethyl)dimethylphosphine oxide was obtained from VeZerf Laborsynthesen, GmbH, Germany.

(Chloromethyl)diphenylphosphine oxide, was prepared from (Hydroxymethyl)-dimethylphosphine oxide (obtained from VeZerf Laborsynthesen, GmbH, Germany) and thionyl chloride (obtained from Aldrich) as described by Qureshi, A. et al., (J. Chem. Res., 1998, 355).

The following chemicals were obtained from Sigma-Aldrich: titanium(IV)isopropoxide; dimethyl 5-hydroxyisophthalate and potassium carbonate.

The following chemicals were obtained from the DuPont Company, Wilmington, Del.: Bio based 1,3-propanediol (Bio-PDO™) and Sorona® Poly(trimethylene terephthalate) (PTT), bright 1.02 IV.

Methods Used to Measure Flame Retardancy

LOI (limited oxygen index) is a measure of the minimum oxygen content needed to sustain candle like burn. LOI can be determined from thermal gravimetric analysis (TGA) in air to limiting oxygen index (LOI) predictions using the following equation:

LOI=0.40×δ+17.5, in which δ is char yield above 700° C.

Char yield is the sample residue at given temperature that is not volatilized during the heat treatment (Krevelen, *Polymer*, 16: 615, 1975; and Li et al., *Polym. Adv. Technol.*, 21: 229, 2010).

Molecular Weight by Size Exclusion Chromatography

A size exclusion chromatography system (Alliance 2695™ from Waters Corporation, Milford, Mass.), was provided with a Waters 414™ differential refractive index detector, a multiangle light scattering photometer DAWN Heleos II (Wyatt Technologies, Santa Barbara, Calif.), and a ViscoStar™ differential capillary viscometer detector (Wyatt). The software for data acquisition and reduction was Astra® version 5.4 by Wyatt. The columns used were two Shodex GPC HFIP-806M™ styrene-divinyl benzene columns with an exclusion limit of $2 \times 10^7$ and 8,000/30 cm theoretical plates; and one Shodex GPC HFIP-804M™ styrene-divinyl benzene column with an exclusion limit $2 \times 10^5$ and 10,000/30 cm theoretical plates.

For analysis, the samples were dissolved in 1,1,1,3,3,3-hexafluoro-2-propanol (HFIP) containing 0.01 M sodium trifluoroacetate by mixing at 50° C. with moderate agitation for four hours followed by filtration through a 0.45 μm PTFE filter. Concentration of the solution was approximately 2 mg/mL.

Data was taken with the chromatograph set at 35° C., with a flow rate of 0.5 ml/min. The injection volume was 100 microliters (μl). The run time was 80 min. Data reduction was performed incorporating data from all three detectors described above. 8 scattering angles were employed with the light scattering detector. No standard for column calibration was involved in the data processing Thermal Analysis Glass transition temperature ($T_g$) and melting point ($T_m$) were determined by differential scanning calorimetry (DSC) performed according to ASTM D3418-08. Thermogravic analysis (TGA) was performed on a TGA Q 500. from TA.

Example 1

Preparation of Dimethyl 5-(((Diphenylphosphoryl)Methoxy)-Isophthalate

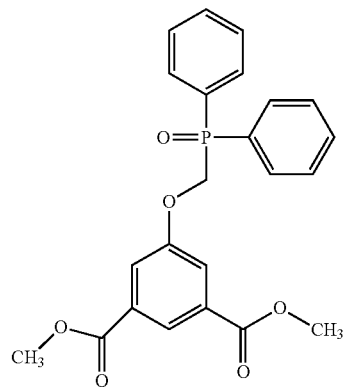 [SMILES: COC(=O)c1cc(OCP(=O)(c2ccccc2)c2ccccc2)cc(C(=O)OC)c1]

In a dry box, dimethyl-5-hydroxy isophthalate (0.525 g, 0.0025 mol), (chloromethyl)diphenylphosphine oxide (0.625 g, 0.0025 mol), potassium carbonate (0.345 g, 0.00125 mol) and ethyl acetate (25.0 mL) were added to an oven dried round bottom flask equipped with a reflux condenser and a stirring bar. The apparatus was removed from the dry box and under nitrogen, the contents were stirred for 48 hours under reflux. The resulting material was cooled and filtered and the filtrate concentrated at reduced pressure. This concentrate was then purified using silica gel column chromatography with hexane/tetrahydrofuran (1:1 by volume to 100% THF) and the eluants material was analyzed by thin layer chromatography using having (hexane/THF (1:1 by volume) as a solvent. The compounds having an Rf of ~0.22 were collected, concentrated at reduced pressure and dried under vacuum affording the desired material, dimethyl 5-((diphenylphosphoryl)methoxy)isophthalate (0.30 g, 29.71% yield). The structure of the product was confirmed using mass spectrometry and nuclear magnetic spectroscopy.

Example 2

Preparation of Dimethyl 5-((Dimethylphosphoryl)Methoxy)Isophthalate

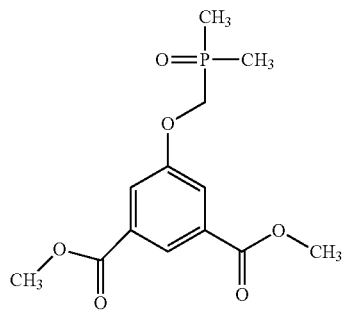

In a dry box, dimethyl-5-hydroxy isophthalate (1.05 g, 0.005 mol), (chloromethyl)dimethylphosphine oxide (0.315 g, 0.0025 mol), potassium carbonate (0.690 g, 0.005 mol) and ethyl acetate (50.0 mL) were added to an oven dried round bottom flask equipped with a reflux condenser and a stirring bar. The apparatus was removed from the dry box and stirred under nitrogen for ~24 hours under reflux. The resulting cooled material was filtered and the filtrate concentrated at reduced pressure. This concentrate was passed through a silica gel column using 5% methanol/tetrahydrofuran as the solvent. The collected fractions were combined and concentrated at reduced pressure and dried under vacuum affording the desired material, dimethyl 5-((dimethylphosphoryl)methoxy)-isophthalate, (0.30 g, ~40.0% yield). The structure of the product was confirmed using mass spectrometry and nuclear magnetic spectroscopy.

Example 3

Preparation of 5-((Dimethylphosphoryl)Methoxy)Isophthalic Acid

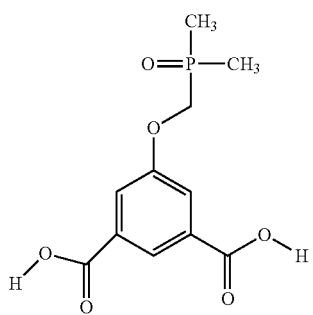 [SMILES: CP(C)(=O)COc1cc(C(=O)O)cc(C(=O)O)c1]

Dimethyl 5-((dimethylphosphoryl)methoxy)isophthalate (0.60 g g, 0.002 mol), potassium hydroxide (1.11 g, 0.7 mol) and water (28.6 mL) were added to a round bottom flask equipped with a reflux condenser and a stirring bar. The resulting mixture was stirred overnight under reflux. The cool reaction mixture was then made strongly acidic with conc. HCl. The precipitated acid was filtered off and dried under vacuum, affording 0.40 g (69.32% yield) of the desired material, 5-((dimethylphosphoryl)methoxy)isophthalic acid.

Example 4

Preparation of Dimethyl 5-((Dimethylphosphoryl)Methoxy)Isophthalate

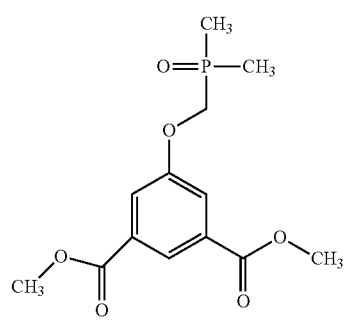

In a dry box, dimethyl-5-hydroxy isophthalate (21.00 g, 0.10 mol), (chloromethyl)dimethylphosphine oxide (6.3 g, 0.05 mol), potassium carbonate (13.8 g, 0.10 mol) and toluene (1.00 L) were added to a oven dried round bottom flask equipped with a reflux condenser and a stirring bar. The apparatus was removed from the dry box and under nitrogen refluxed for ~13 days. The resulting cooled material was filtered and the filtrate concentrated at reduced pressure. This concentrate was then column chromatographed with 5% methanol/tetrahydrofuran. The collected fractions were combined and concentrated at reduced pressure and dried under vacuum affording dimethyl 5-((dimethylphosphoryl)methoxy)isophthalate_(8.75 g, 58.30% yield). The structure of the product was confirmed using mass spectrometry and nuclear magnetic spectroscopy.

Example 5

Char Yield of Homopolymer from 1,3-Propanediol and Dimethyl 5-((Dimethylphosphoryl)Methoxy)-Isophthalate Dimethyl 5-((dimethylphosphoryl)methoxy)isophthalate was prepared as described in Example 4.

Preparation of Copolymer of 1,3-propanediol and dimethyl 5-((dimethyl-phosphoryl)methoxy)-isophthalate

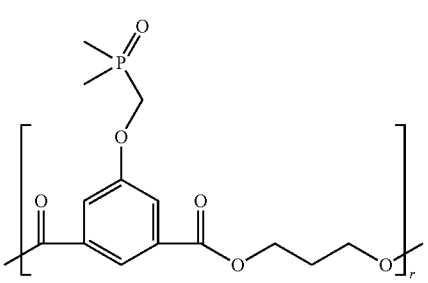

Dimethyl 5-((dimethylphosphoryl)methoxy)-isophthalate (72.9 g, 0.24 mol), and 1,3-propanediol (33.3 g, 0.43 mol) were charged to a pre-dried 250 mL three necked round bottom flask. An overhead stirrer and a distillation condenser were attached. The reactants were stirred at a speed of 10 revolutions per minute (rpm) and the reaction mass was kept under nitrogen$_{(g)}$ (N$_2$) purge atmosphere, the condenser was kept at 23° C. The contents were degassed three times by evacuating down to 500 mTorr and refilling back with N$_2$ gas. Titanium(IV)isopropoxide catalyst (88 mg) was added after the first evacuation. The flask was immersed into a preheated metal bath set at 160° C. The solids were allowed to completely melt at 160° C. for 20 minutes and the stirrer speed slowly increased to 180 rpm. The temperature was increased to 210° C. and maintained for 90 minutes to distill off most of the formed methanol. The nitrogen purge was closed and a vacuum ramp started, after about 60 minutes the vacuum reached a value of 50-60 mTorr, and the reaction held for 3 hours. The over head stirrer was stopped and elevated from the floor of the reaction vessel before the vacuum was turned off and the system purged with N$_2$ gas. The formed product was allowed to cool to ambient temperature and the reaction vessel was removed and the product recovered after carefully breaking the glass with a hammer. Yield: ~65 g (86%). M$_n$ (SEC)~1 400D, PDI~1.39. Char yield of copolymer of dimethyl 5-((dimethylphosphoryl)methoxy)-isophthalate formed in (B) prepared above was compared with Sorona® bright 1.02 IV (CE-A) and results are shown in Table 1 below.

TABLE 1

Comparison of char yield of copolymer formed in B with Sorona ® bright 1.02 IV (CE-A)

| Sample | Residual char at 700° C. (%)[1] | Estimated LOI[2] |
| --- | --- | --- |
| copolymer of Dimethyl 5-((dimethyl-phosphoryl)methoxy)-isophthalate | ~13 | ~22.7 |
| CE-A Comparative example 1 which is Sorona bright control, stated above. | 0 | ~17.5 |

[1]From TGA analysis in air.

[2]From equation: LOI = 0.40 × δ + 17.5* in which δ is char yield above 700° C.

As shown in Table 1, The char yield of copolymer of dimethyl 5 ((dimethylphosphoryl) methoxy)-isophthalate at 700° C. is ~13% indicating a char forming ability of the polymer.

Example 6

Copolymer from 1,3-Propanediol, Dimethylterephthalate, and Dimethyl 5-((Dimethylphosphoryl)Methoxy)-Isophthalate Dimethyl 5-((dimethylphosphoryl)methoxy)isophthalate was prepared as described in Example 4.

Preparation of Copolymer of 1,3-propanediol, dimethylterepthalate, and dimethyl 5-((dimethylphosphoryl)methoxy)-isophthalate

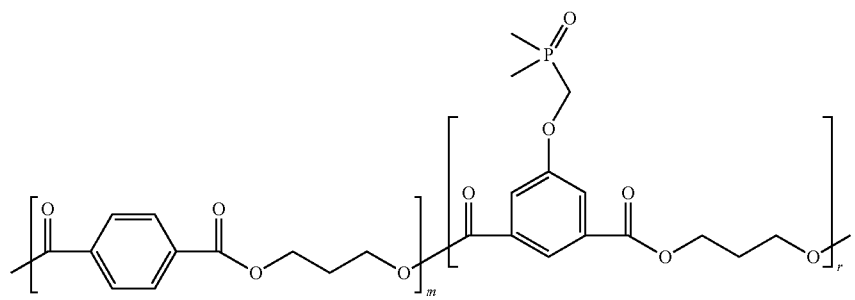

Dimethylterephtalate (DMT, 60 g, 0.309 mmol), dimethyl 5-((dimethylphosphoryl)-methoxy)-isophthalate (3 g, 0.01 mol, 5 wt % to DMT), and 1,3-propanediol (42.4 g, 0.55 mol) were charged to a pre-dried 500 mL three necked round bottom flask. An overhead stirrer and a distillation condenser were attached. The reactants were stirred at a speed of 50 rpm and the reaction mass was kept under nitrogen$_{(g)}$ (N$_2$) purge atmosphere, the condenser was kept at 23° C. The contents were degassed three times by evacuating down to 100 Torr and refilling back with N$_2$ gas. Titanium (IV)isopropoxide (20 mg) was added after the first evacuation. The flask was immersed into a preheated metal bath set at 160° C. The solids were allowed to completely melt at 160° C. for 20 minutes after which the stirring speed was slowly increased to 180 rpm. The temperature was increased to 210° C. and maintained for 60 minutes to distill off the formed methanol. The temperature was increased to 250° C. after which the nitrogen purge was closed and a vacuum ramp started, after about 60 minutes the vacuum reached a value of 50-60 mTorr. The reaction was held for 3 hours after which the polymerization was stopped by removing the heat source. The over head stirrer was stopped and elevated from the floor of the reaction vessel before the vacuum was turned off and the system purged with N$_2$ gas. The formed product was allowed to cool to ambient temperature and the reaction vessel was removed and the product recovered after carefully breaking the glass with a hammer. Yield ~90% off white solid. The product was characterized by $^1$H and $^{31}$P NMR providing the following details: $^1$H-NMR (tce-d2) δ: 8.30 (s, ArH, 1H), 8.20-7.90 (m, ArH, 4H), 7.80 (s, ArH, 2H), 7.65 (s, ArH, cyclic dimer), 4.65-4.40 (m, —CH$_2$—COO—, 4H), 4.30 (m, 2H, —O—CH$_2$—P), 4.80 (m, 2H, —CH$_2$—OH), 4.60 (m, DPG, 4H), 2.30-2.15 (m, —CH$_2$—, 2H), 2.05 (m, DPG, 4H), 1.5 (m, 6H, —$CH_3$). $^{31}$P-NMR (tce-d2) δ ppm: 39. $M_n$ (SEC)~22 400D, PDI~2.02. $T_m$ (DSC)~226° C., $T_g$~57° C.

What is claimed is:

1. A composition comprising a (phosphonyl) aromatic compound represented by the structure (I)

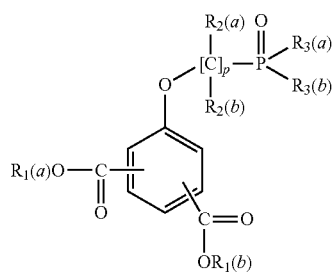

Wherein, $R_1(a)$ and $R_1(b)$ are each independently H, $C_nH_{2n+1}$, phenyl or benzyl;

$R_2(a)$ and $R_2(b)$ are each independently H, $C_nH_{2n+1}$, phenyl or benzyl with the proviso that no more than one $R_{2(a)}$ and no more than one $R_{2(b)}$ can be phenyl or benzyl;

$R_3(a)$ and $R_3(b)$ are each independently $C_nH_{2n+1}$, phenyl or benzyl;

n is an integer of 1-10;

and, p is an integer of 1-10.

2. The composition of claim 1 wherein $R_1(a)$ and $R_1(b)$ are the same.

3. The composition of claim 1 wherein $R_2(a)$ and $R_2(b)$ are the same.

4. The composition of claim 1 wherein $R_3(a)$ and $R_3(b)$ are the same.

* * * * *